US012765899B2

(12) United States Patent
Batiste et al.

(10) Patent No.: US 12,765,899 B2
(45) Date of Patent: Oct. 20, 2026

(54) ATRAUMATIC THROMBECTOMY DEVICE

(71) Applicants: Stanley Batiste, Granite Bay, CA (US); Daniel Batiste, Granite Bay, CA (US)

(72) Inventors: Stanley Batiste, Granite Bay, CA (US); Daniel Batiste, Granite Bay, CA (US)

( * ) Notice: Subject to any disclaimer, the term of this patent is extended or adjusted under 35 U.S.C. 154(b) by 374 days.

(21) Appl. No.: 18/196,998

(22) Filed: May 12, 2023

(65) Prior Publication Data

US 2023/0363778 A1 Nov. 16, 2023

Related U.S. Application Data

(60) Provisional application No. 63/341,974, filed on May 13, 2022.

(51) Int. Cl.
*A61B 17/221* (2006.01)
*A61B 17/00* (2006.01)
*A61B 17/22* (2006.01)

(52) U.S. Cl.
CPC .. *A61B 17/221* (2013.01); *A61B 2017/00367* (2013.01); *A61B 2017/22084* (2013.01)

(58) Field of Classification Search
CPC ........ A61B 17/221; A61B 2017/00367; A61B 2017/22084; A61B 2017/00287; A61B 17/32056; A61B 2017/00358
See application file for complete search history.

(56) References Cited

U.S. PATENT DOCUMENTS

| | | | | |
|---|---|---|---|---|
| 6,419,639 | B2 * | 7/2002 | Walther | A61B 17/00234 606/174 |
| 6,866,651 | B2 * | 3/2005 | Constantz | A61B 17/22 606/127 |
| 7,875,051 | B2 * | 1/2011 | Beulke | A61F 2/01 606/200 |
| 2020/0085453 | A1 * | 3/2020 | Porter | A61M 25/0082 |
| 2021/0000494 | A1 * | 1/2021 | Kitaoka | A61B 17/221 |

* cited by examiner

*Primary Examiner* — Kathleen S Holwerda
*Assistant Examiner* — James R Mcginnity
(74) *Attorney, Agent, or Firm* — Heisler & Associates

(57) ABSTRACT

An atraumatic thrombectomy device for use in removing a clot from a vessel of a patient is provided. The device includes a handle configured to be located exterior to the patient, a knob rotatably coupled to the handle and configured to be located exterior to the patient, a net, a first rod coupled to the knob and the net, and a second rod coupled to the handle and the net. The net is configured to move between a collapsed position and an open position. The net is configured to encapsulate the clot within the vessel of the patient when in the open position. Responsive to the knob rotating with respect to the handle, the first rod is configured to rotate between a first position corresponding to the net being in the collapsed position and a second position corresponding to the net being in the open position.

19 Claims, 7 Drawing Sheets

10

100
101
201
211
210
300
221
220
200
101
201
400
211
200
100
210

10

200,201,400,210,211
10
100
101

400
211
201
210
200

2

10
240
600
500
400
211
210
100
200,201,210,211

Figure 4A
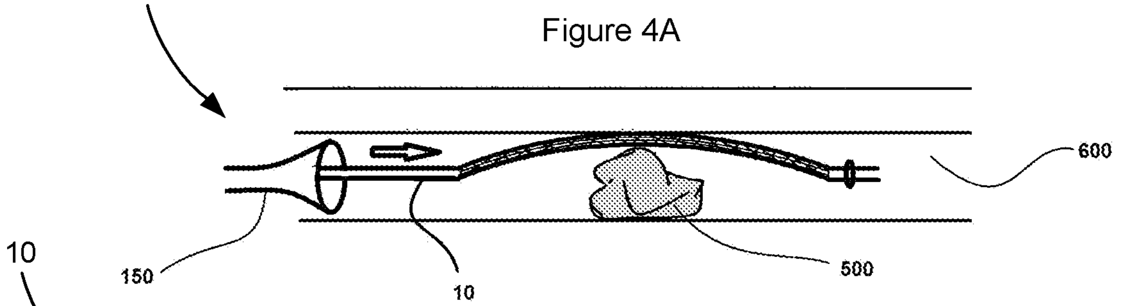
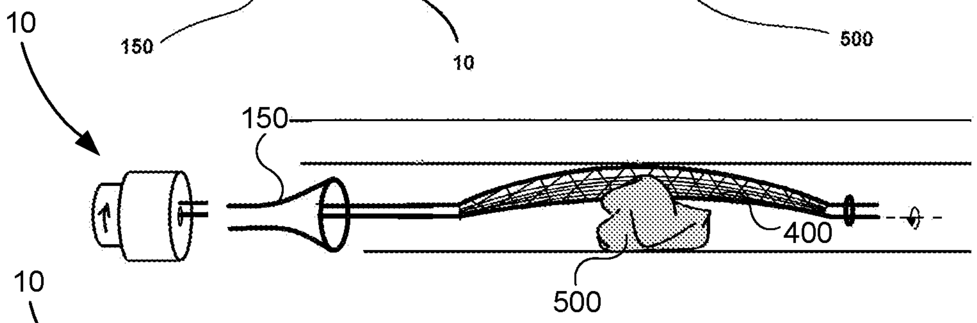
Figure 4B
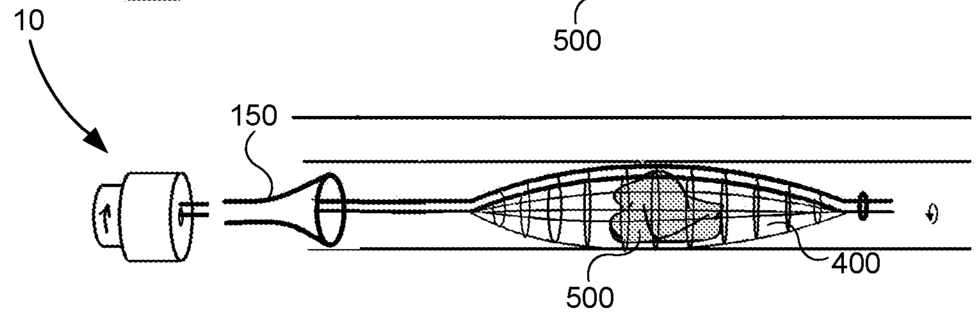
Figure 4C
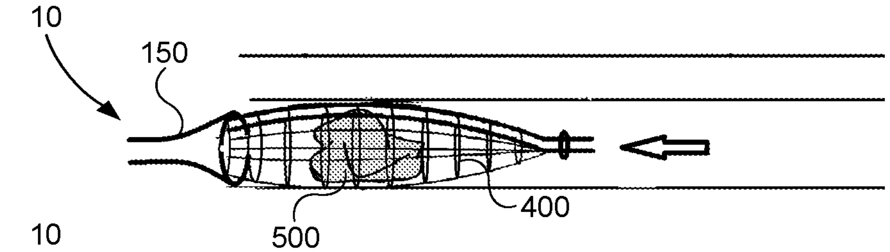
Figure 4D
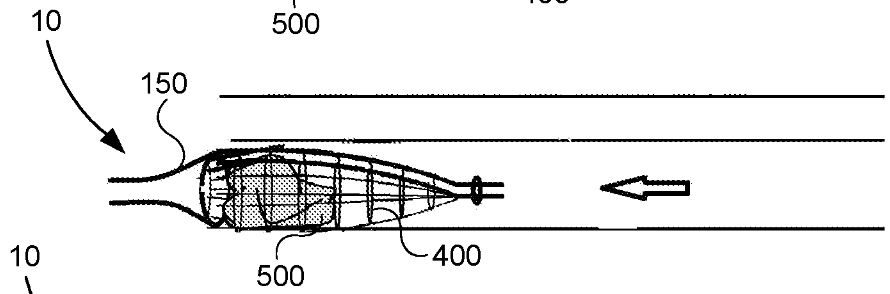
Figure 4E
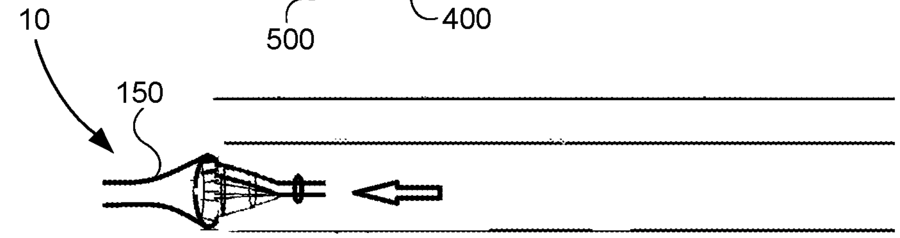
Figure 4F

ATRAUMATIC THROMBECTOMY DEVICE

1. FIELD OF THE INVENTION

The present invention relates to thrombectomy devices which are used in the human vascular system to remove blood clots.

2. BACKGROUND

Deep vein thrombosis (DVT) is a common problem and causes significant morbidity and mortality in the United States and throughout the world. DVT is caused when a blood clot forms in the deep veins of the legs. These blood clots typically occur due to slow or reduced blood flow through the deep veins such as when the patient cannot ambulate or otherwise efficiently circulate their blood. Another cause of inefficient circulation may be due to structural damage to the veins such as general trauma or after surgical procedures. Additionally, a blood clot may form in a deep vein due to a particular medical condition or a propensity for the patient to have a hypercoagulability state. For example, a woman on birth control who smokes has an increased risk of forming blood clots and is thus predisposed to DVT.

The result and clinical significance of DVT is when the clot breaks free from its location in the deep vein of the leg, the clot travels through the circulatory system and may eventually lodge in a location that is averse to the patient's health. For example, the clot may dislodge from a location in the deep vein of the patient's leg and migrate through the heart and come to rest in the patient's lung, thereby causing a pulmonary embolism (PE) resulting in restricted circulation, which can cause sudden death for the patient.

DVT & PE are currently prevented in several ways including anticoagulation therapy, thrombectomy, thrombolysis and inferior vena cava filter (IVC filter) placement. Anticoagulation therapy utilizes various medications that reduce the patient's propensity for forming blood clots.

Thrombolysis is a medical technique that is performed for treatment of a DVT, in which various medicines are infused into the region of the clot that subsequently causes the clot to dissolve. This form of treatment has the disadvantage that the medication may cause bleeding at other sites such as within the brain. For example, if a patient has previously had a minute non-clinical stroke, the medication used in a thrombolysis may cause a previously healed vessel to bleed within the patient's head.

Thrombectomy is a procedure generally performed for treatment of a DVT, in which a blood clot is extracted from the vein using a surgical procedure or by way of an intravenous catheter using a mechanical aspiration or extraction method. This form of treatment can be technically challenging as the catheter has to be steered or navigated to a specific location in order to extract the clot. Currently, there are many different types of mechanical thrombectomy devices using several different means of clot removal. Extraction devices use expanding, claw shaped removal stents and filter types of devices that trap clots, which are then pulled out of the body through the original vascular entry point. With aspiration devices, a means of creating low pressures and suction through a catheter may be used. A second type of aspiration catheter utilizes a high velocity jet directed back into the catheter to create low pressure and suction using the Bernoulli principle. Both aspiration methods can remove clots out of vessels, but are limited because once the majority of the clot is removed, blood replaces the space such that these catheters then mainly aspirate blood, thereby making it difficult to suction the clot out. Challenges with blood loss during aspiration limits the duration aspiration can occur and the amount of clot that can be removed.

It is with respect to these and other considerations that the instant disclosure is concerned.

SUMMARY

Deep vein thrombosis (DVT) is a common problem and causes significant morbidity and mortality in the United States and throughout the world. DVT is caused when a blood clot forms in the deep veins of the legs. Currently therapy involves using pharmacological and/or mechanical means of removing the clot from the vessels. With mechanical thrombectomy clot is removed by several means including trapping the clot in a mesh or stent type system and pulling it out. Although this can be effective in clot removal, many of the devices today rely on mechanism which put pressure and friction on the vessel walls and can damage the valves. It has been shown that this pressure and friction can cause damage to the vessels and later lead to scaring and vessel occlusion. The ideal thrombectomy device would extract the clot and be atraumatic to the vessel walls and the valves.

The disclosed innovation solves the noted issues by creating a net around the clot without creating abrasion on the walls of the veins or pressures pulling on the valves. The device utilizes two rods, which may be curved, and of which one which may be static, and the other which may be rotatable around an axis, such as a central axis. Connecting the two rods is a stent-type netting that expands to capture the clot. The rods are introduced into the patient's vein and positioned within or to the side of the clot. The curvature of the two aligned rods will gently oppose the vessel wall (e.g., be concave facing away from the wall of the vessel). One rod is stationary, and the second rod is rotated gently carrying the netting material along a lining the outer wall of the vessel. In one example, a 360 degree turn of the rotatable rod causes the rods to again oppose each other, such that the netting of the clot is complete. The entire apparatus may then be removed, along with the clot through the original vessel entry point.

Another example embodiment of the disclosed concept provides for a device which includes a hollowed out rod that has many side holes for medication infusion. During the thrombectomy procedure, thrombolytic or other medication can be infused to bathe the inner lumen of the vein and indwelling clot. This injection could be in the drip/slow infusion method or as a fast pulse/spray technique.

Other systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The components in the figures are not necessarily to scale, emphasis instead being placed upon illustrating the principles of the invention. In the figures, like reference numerals designate corresponding parts throughout the different views.

FIG. 4A, FIG. 4B, FIG. 4C, FIG. 4D, FIG. 4E and FIG. 4F show the atraumatic thrombectomy device according to FIG. 1A, FIG. 1B, and FIG. 1C, deployed within a vessel of a patient, and in first, second, third, fourth, fifth, and sixth positions, respectively, with respect to a vessel entry sheath.

DISCUSSION OF INVENTION

As employed herein, the term "coupled" shall mean connected together either directly or via one or more intermediate parts or components.

In the following description, numerous specific details are set forth in order to provide a more thorough description of the present invention. It will be apparent, however, to one skilled in the art, that the present invention may be practiced without these specific details. In other instances, well-known features have not been described in detail so as not to obscure the invention.

Figures 1A, 1B, 1C:
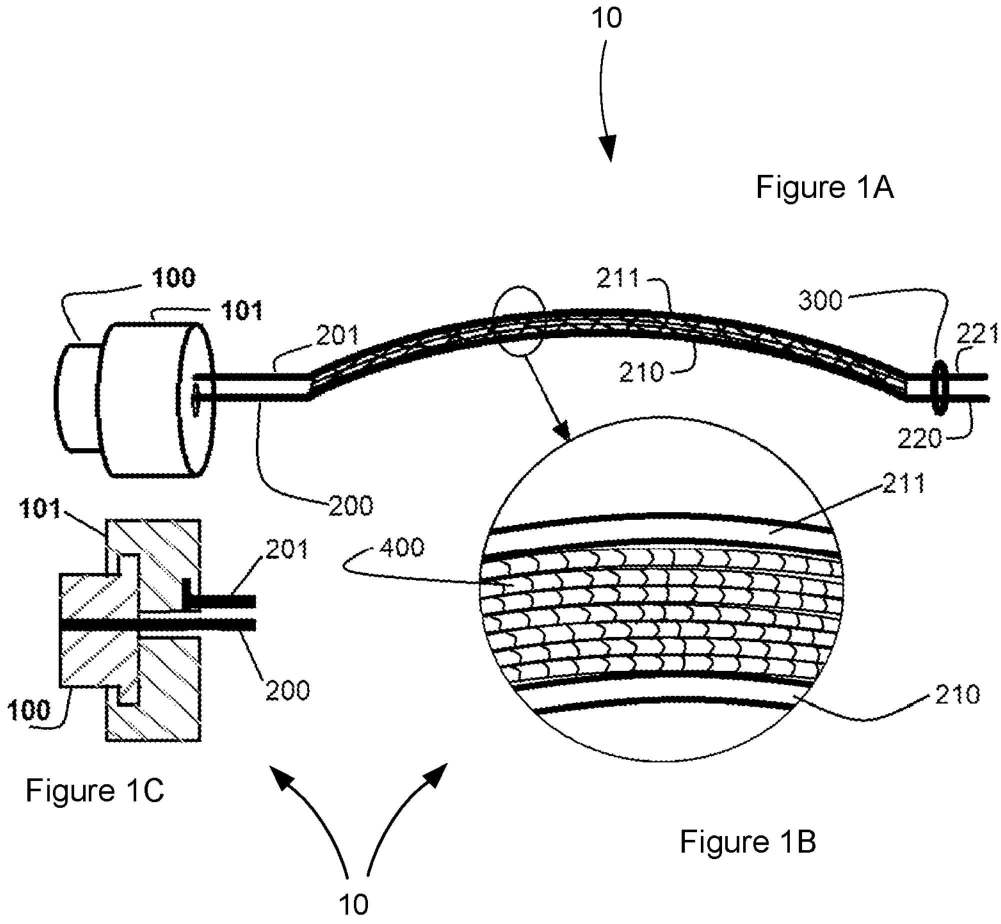
FIG. 1A, FIG. 1B, and FIG. 1C show isometric, enlarged, and section views, respectively, of an atraumatic thrombectomy device, in accordance with one non-limiting embodiment of the disclosed concept.

An atraumatic thrombectomy device 10 is shown in FIGS. 1A-1C. The device 10 is configured for use in removing a clot from a vessel of a patient. In one example, the device 10 may include a rotating inner knob 100 inset within a stationary outer round handle 101, the knob 100 and handle 101 being examples of grippable structures. In one example, the knob 100 is rotatably coupled to the handle 101 and is configured to be located exterior to a patient. As shown, the device 10 further includes a first rod (e.g., rotating rod 200), a second rod (e.g., static rod 201), and a clot capture net 400. As will be discussed in greater detail below, the net 400 may be configured to move between a collapsed position and an open position, wherein the net 400 is configured to encapsulate (e.g., fully surround on all sides) a clot within a vessel of a patient when in the open position.

The rotating knob 100 is fixed to (e.g., coupled to) the rotating rod 200 and the stationary outer handle is fixed to (e.g., coupled to) the static rod 201. Furthermore, the rods 200, 201 are preferably coupled to the net 400. Additionally, both of the rods 200, 201 include a proximal first linear segment 204, 205, the length of which allows entry into the vessel, and a curved segment 210, 211 extending from the first linear segment 204, 205. In one example, the rods 200, 201 further include a short second linear segment 220, 221 extending from an opposing end of the curved segments 210, 211 such that the curved segments 210, 211 extend from the first linear segments 204, 205 to the second linear segments 220, 221.

Additionally, as shown, the first linear segments 204, 205 are preferably located parallel to each other and are each preferably coupled to a corresponding one of the knob 100 and the handle 101. Moreover, the curved segments 210, 211 are also preferably located parallel to each other, and the second linear segments 220, 221 are preferably located parallel to each other. In this manner, the device 10 is advantageously configured to be inserted into a vessel of a patient and allow for proper capture of a clot, as will be discussed below, such as with the curved segments 220, 221 being located in the vessel of the patient to capture the clot.

As stated above, the rods 200, 201 are linked by a clot capture net 400 which can be compact for initial vessel entry and future removal depending on the position of the rods. The distal linear segments 220, 221 of the rods are preferably linked by a coupling member (e.g., constriction ring 300) which allows rotation but keeps the rods 200, 201 aligned. Stated differently, the constriction ring 300 connects the distal linear segments 220, 221 (e.g., the linear segments 220, 221 are preferably bounded by the ring 300) to each other in order to allow rotation of the rotating rod 200 while maintaining alignment between the first and second rods 200, 201.

Figures 2A, 2B, 2C, 2D, 2E, 2F, 2G:
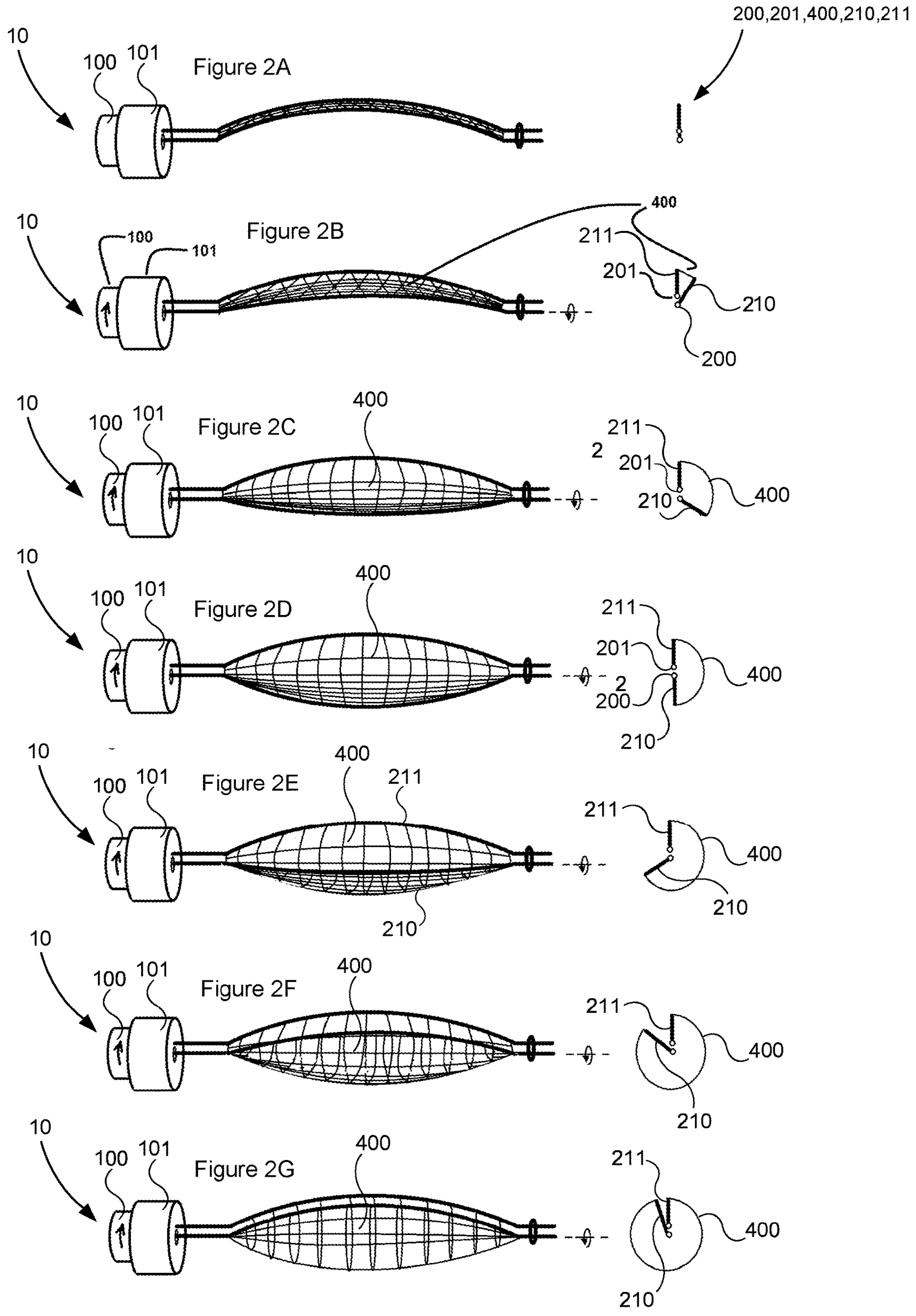
FIG. 2A, FIG. 2B, FIG. 2C, FIG. 2D, FIG. 2E, FIG. 2F, and FIG. 2G show isometric views of the atraumatic thrombectomy device according to FIGS. 1A, 1B, and 1C, and are shown with the net in first, second, third, fourth, fifth, sixth, and seventh positions, respectively.

Operation of the device is shown on FIGS. 2A-2G, which shows the device 10 in different positions. In FIG. 2A the device 10 is shown with the net 400 in a collapsed position with the rods 200, 201. In FIG. 2B the rotating knob 100 is shown turned one-quarter turn and the rotating rod 200 moves apart from or relative to the static rod 201 in a circular motion. This in turn moves the curved segment 210 in relation to the other curved segment 211 thereby extending the net 400 while the curved segment may slightly brush or scrape the inner surface of the vessel 600 (FIG. 3). The capture net 400 is now slightly open. In FIGS. 2B through 2G, the rotating knob 100 is rotated further (e.g., thereby rotating the rotating rod 200), opening the circular capture net 400 until the rods 200, 201 are again opposing each other (e.g., without limitation, are abutting).

Accordingly, responsive to the knob 100 rotating with respect to the handle 101, the rotating rod 200 is configured to rotate between a first position (FIG. 2A) corresponding to the net being in the collapsed position and a second position (FIG. 2G) corresponding to the net being in the open position. Although the net 400 is shown in seven different positions in FIGS. 2A-2G, it will be appreciated that the net 400 may have any number of positions as it is opened to capture the clot. More specifically, when the rotating rod 200 rotates from the first position (FIG. 2A) to the second position (FIG. 2G), the first rod rotates at least 350 degrees, and more preferably rotates at least 360 degrees in order to fully encapsulate (e.g., surround on all sides) the clot within the net 400.

Figures 3A, 3B, 3C, 3D, 3E, 3F, 3G:
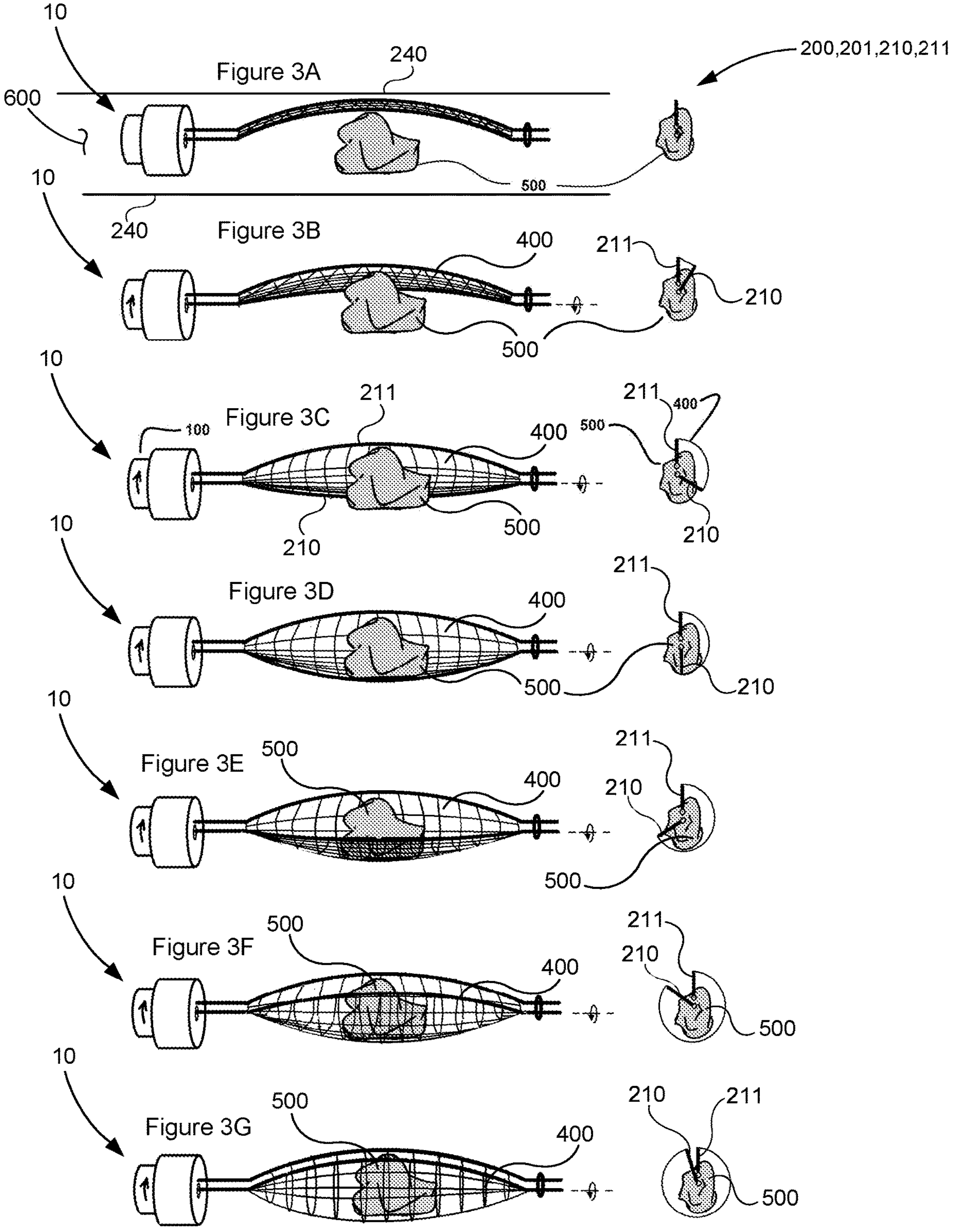
FIG. 3A, FIG. 3B, FIG. 3C, FIG. 3D, FIG. 3E, FIG. 3F, and FIG. 3G, show other isometric views of the atraumatic thrombectomy device according to FIG. 1A, FIG. 1B, and FIG. 1C, with the net in first, second, third, fourth, fifth, sixth, and seventh positions, respectively, and with a clot shown in simplified form.

Capturing of clot with the device is illustrated in FIGS. 3A-3G. As shown in FIG. 3C, as the rotating knob 100 is turned, the capture net 400 moves to cover the clot 500. In FIG. 3G the clot 500 is entirely encircled by the capture net and is ready to be removed. Additionally, the device 10 is advantageously uniquely constructed to ensure that the clot 500 does get captured. FIG. 3A also shows the vessel interior space 600 and the vessel walls 240.

More specifically, and referring again to FIG. 1A, the first linear segments 204, 205 and the second linear segments 220, 221 of the first and second rods 200, 201 extend from the curved segments 210, 211 of the first and second rods 200, 201 at corresponding junctions 206, 207, 222, 223, and as shown, the net 400 preferably extends from each of the corresponding junctions 206, 207, 222, 223 in order to allow the clot to be encapsulated by the net in the open position. In other words, substantially or entirely the entire length of the curved segments 210, 211 are overlayed by the capture net 400, such that the relatively wide opening in the region of the curved segments 210, 211 created by the rotation of the rotating knob 100 is configured to encapsulate and capture the clot.

FIGS. 4A-4F illustrate clot capture within a patient's vessel 600 and clot removal. In one example, the curved segments 210, 211 are configured to oppose (e.g., be concave facing away from) a wall of the vessel 600 of the patient, thereby safely allowing the device to be inserted and removed from the vessel 600 of the patient. The device 10 is advanced through the vessel entry sheath 150 to the clot. As previously described, the clot 500 is encircled and captured. The device 10 and the clot 500 is then removed by pulling it out of the patient through the sheath 150.

In one example, a thrombectomy method includes providing the device 10, positioning the handle 101 and the knob 100 exterior to a patient, inserting the rods 200, 201 and the net 400 into an interior of a vessel 600 of the patient proximate to a clot 500, and rotating the knob 100 with respect to the handle 101 in order to cause the rotating rod 200 to rotate between a first position corresponding to the net 400 being in a collapsed position and a second position corresponding to the net 400 being in an open position, the collapsed position corresponding to the clot 500 not being encapsulated within the net 400, and the open position corresponding to the net 400 encapsulating the clot 500 within the vessel 600.

In one example, the method further includes inserting a sheath 150 into the interior of the vessel 600, and the aforementioned step of inserting the rods 200, 201 and the net 400 includes inserting the rods 200, 201 and the net 400 through the sheath 150. Additionally, the method may also include the steps of removing the rods 200, 201 and the net 400 with the encapsulated clot 500, out of the vessel 600 of the patient through the sheath 150, and removing the sheath 150 from the vessel 600 of the patient.

Figure 5A:
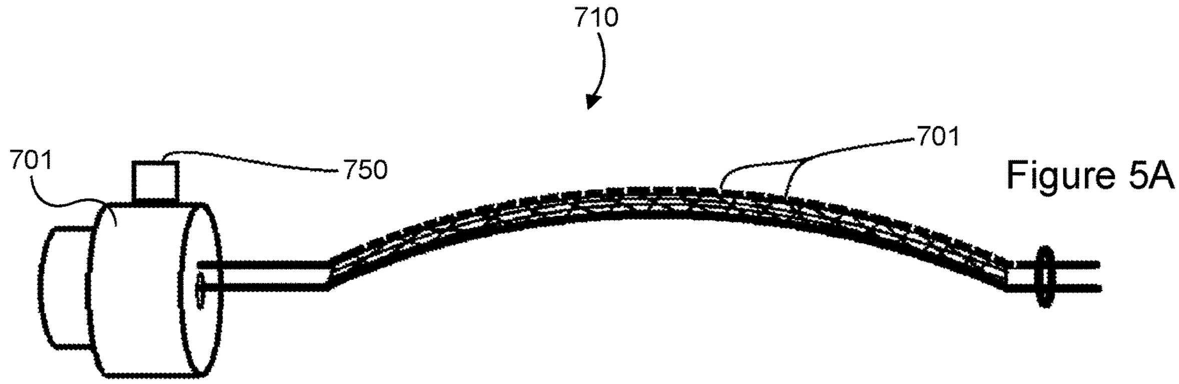
FIG. 5A and FIG. 5B show isometric and section views, respectively, of another atraumatic thrombectomy device, according to another non-limiting embodiment of the disclosed concept.
Figure 5B:
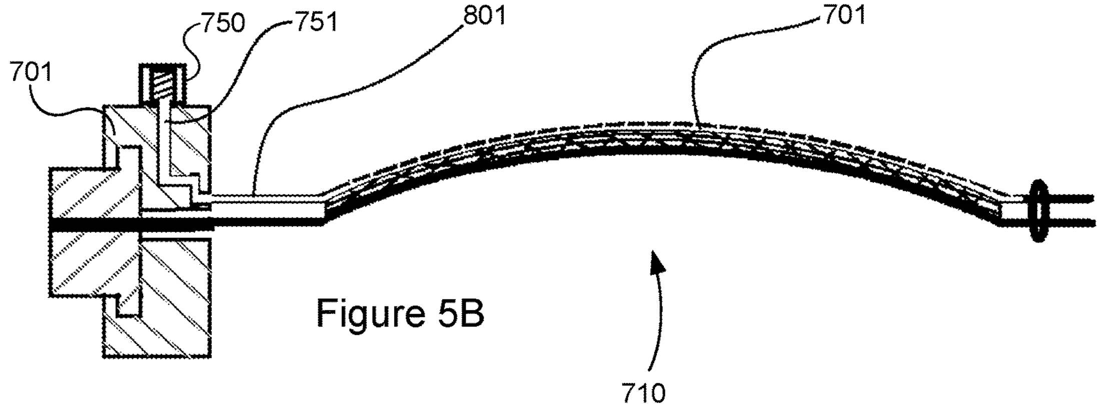
Figure 6:
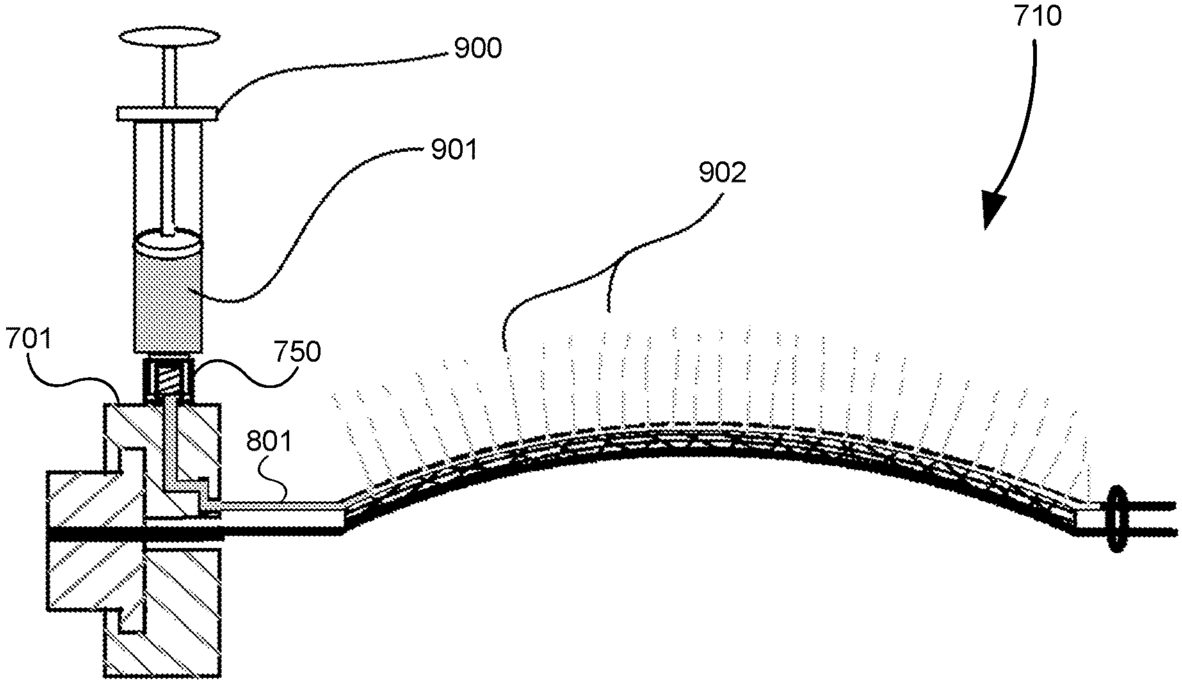
FIG. 6 shows the device of FIGS. 5A and 5B coupled to a syringe.

FIGS. 5A-6 show another atraumatic thrombectomy device 710, in accordance with another non-limiting embodiment of the disclosed concept. The device 710 is similar to the device 10, discussed above, and like numbers represent like features. As shown in FIG. 5A, a luer lock or other fluid attachment port 750 is located on the inner handle 701 and has a continuous channel 751 (FIG. 5B) through the handle 701, which then continues to the static rod 801, and further to the main length of the static rod 801. In other words, the static rod 801 can generally be understood as having a continuous channel throughout its length which connects to (e.g., is in fluid communication with) a channel 751 that extends through the handle 701. Furthermore, in one example, this fluid pathway then continues and connects with the numerous side holes in the static rod 801. The channels in the handle 701 and the static rod 801 are configured to receive medication for delivery to the clot (e.g., the clot 500 shown in FIGS. 4A-4E) via the holes in the static rod 801. Stated differently, the channel 751 of the handle 701 extends through the handle 701 and is in fluid communication with the channel of the static rod 801 in order to allow the medication to be delivered through the handle 701 to the channel of the static rod 801.

FIG. 6 shows operation of the example device 710. As shown, a syringe 900 containing medication 901 is connected to the fluid attachment port 750 and is injecting fluid through the channel 751 of the handle 701, through the channel of the rod 801, and out the side holes. Fluid 902 is then shown exiting the side holes. In this manner, the syringe 900 injects the medication 901 through the channels of the handle 701 and the static rod 801, and through the through holes of the static rod 801 (e.g., and into the clot). In this manner, the aforementioned method may further include delivering the medication 901 to the clot via the channel 751 of the handle 701, the channel of the static rod 801, and the holes of the static rod 801. The method may also further include connecting the syringe 900 containing the medication 901 to the attachment port 750, and actuating the syringe 900 to inject the medication 901 through the channel 751 of the handle 701, the channel of the static rod 801, and through the holes of the static rod 801.

Although the example of FIGS. 5A-6 has been described in association with the static rod 801 having a channel and a plurality of holes in order to allow medication to be passed therethrough and to break up the clot, it will be appreciated that a suitable alternative rotating rod could likewise be configured with a channel and holes to allow medication to travel through, without departing from the scope of the disclosed concept.

Figures 7A, 7B:
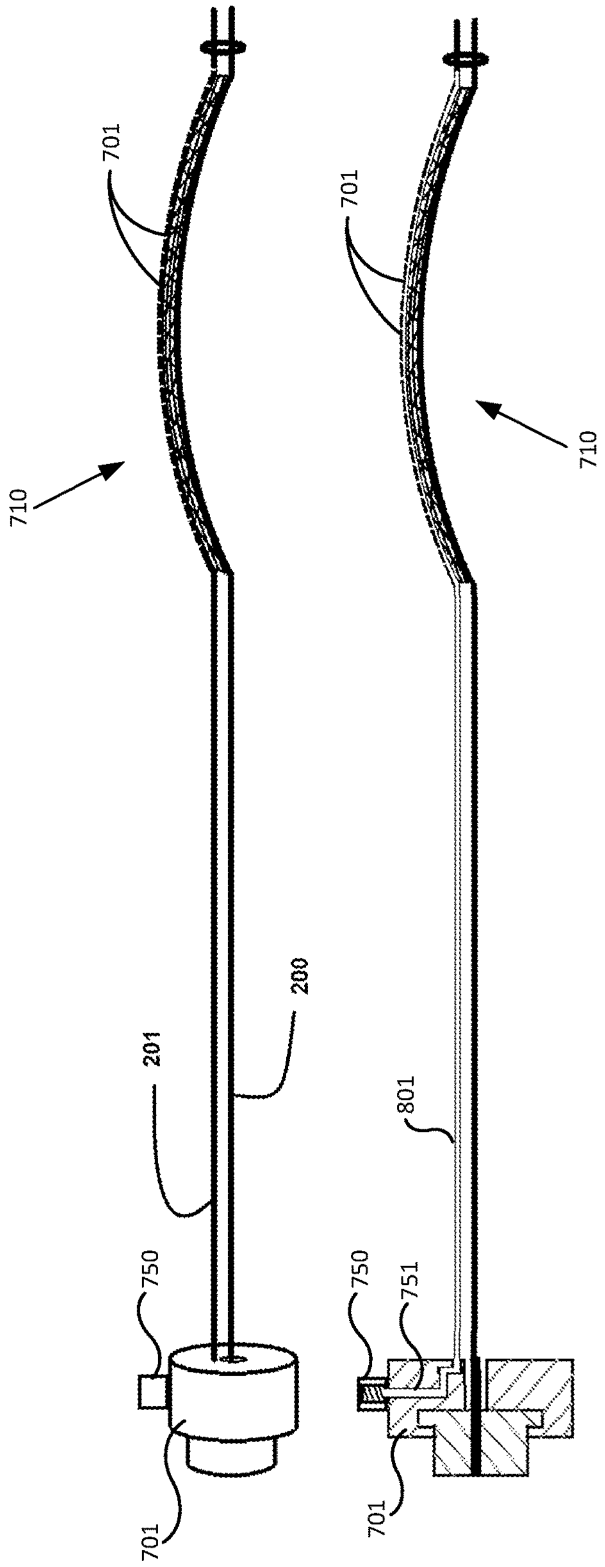
FIG. 7A and FIG. 7B illustrate an alternative embodiment showing elongated rods 200, 201.

FIGS. 7A and 7B illustrate an alternative embodiment showing elongated rods 200, 201. As compared to the other figures, similar elements are labeled with identical reference numbers and only the new aspects are discussed. In this embodiment, the rods 200, 201 are longer thereby extending the reach of the first curved segment 210 and the second curved segment 211. It is contemplated that the device may be supplied with rods of various lengths thereby allowing the doctor to choose the best length medical device for the procedure. In other embodiments, the rods 201, 200 may be adjustable in length.

While various embodiments of the invention have been described, it will be apparent to those of ordinary skill in the art that many more embodiments and implementations are possible that are within the scope of this invention. In addition, the various features, elements and embodiments described herein may be claimed or combined in any combination or arrangement.

What is claimed is:

1. An atraumatic thrombectomy device for use in removing a clot from a vessel of a patient, the atraumatic thrombectomy device comprising:

a handle configured to be disposed exterior to the patient;

a knob rotatably coupled to the handle and configured to be disposed exterior to the patient;

a net configured to move between a collapsed position and an open position, the net being configured to encapsulate the clot within the vessel of the patient when in the open position;

a first rod coupled to the knob and the net; and a second rod coupled to the handle and the net, wherein each of the first and second rods comprise a linear segment and a curved segment extending from the linear segment, the linear segment of the first rod being disposed parallel to the linear segment of the second rod, the linear segment of the first rod being connected to the knob, the linear segment of the second rod being connected to the handle, the curved segment of the first rod being disposed parallel to the curved segment of the second rod, the curved segment of each of the first and second rods being configured to be disposed in the vessel of the patient, wherein, responsive to the knob rotating with respect to the handle, the first rod is configured to rotate between a first position corresponding to the net being in the collapsed position and a second position corresponding to the net being in the open position;

each of said rods extending from first ends to second ends, said second ends of said rods opposite said first ends;

said net closer to said second ends of said rods than to said first ends of said rods;

at least one of said rods being a rotating rod shaped to follow an orbital path for at least a portion of said rotating rod where said net is coupled thereto, when said rotating rod is rotated about a central axis of said rotating rod;

wherein said pair of rods are coupled at said second ends of said pair of rods in a manner allowing rotation between said pair of rods while holding said second ends of said pair of rods adjacent to each other; and said second ends each including parallel linear segments, said parallel linear segments also parallel with an axis of rotation of said rotating rod.

2. The atraumatic thrombectomy device according to claim 1, wherein at least one of the first and second rods has a channel and a plurality of holes, and, wherein the channel is configured to receive medication for delivery to the clot via the plurality of holes.

3. The atraumatic thrombectomy device according to claim 2, wherein the at least one of the first and second rods is the second rod, and wherein the handle has a channel extending therethrough and in fluid communication with the channel of the second rod in order to allow the medication to be delivered through the handle to the channel of the second rod.

4. The atraumatic thrombectomy device according to claim 3, further comprising an attachment port disposed on the handle and configured to be connected to a syringe containing the medication such that the syringe injects the medication through the channels of the handle and the second rod and through the plurality of holes of the second rod.

5. The atraumatic thrombectomy device according to claim 1, wherein the curved segment of the first rod and the curved segment of the second rod are configured to oppose a wall of the vessel of the patient.

6. The atraumatic thrombectomy device according to claim 1, wherein the coupling member is a ring, and wherein the second linear segment of the first rod and the second linear segment of the second rod are bounded by the ring.

7. The atraumatic thrombectomy device according to claim 1, wherein the first linear segments and the second linear segments of the first and second rods extend from the curved segments of the first and second rods at corresponding junctions, and wherein the net extends from each of the corresponding junctions in order to allow the clot to be encapsulated by the net in the open position.

8. A thrombectomy device, comprising in combination:

a pair of elongate rods including a first rod and a second rod;

each of said rods extending from first ends to second ends, said second ends of said rods opposite said first ends;

a net between said first rod and said second rod and coupled to said first rod and said second rod;

said net closer to said second ends of said rods than to said first ends of said rods;

at least one of said rods being a rotating rod shaped to follow an orbital path for at least a portion of said rotating rod where said net is coupled thereto, when said rotating rod is rotated about a central axis of said rotating rod;

wherein said pair of rods are coupled at said second ends of said pair of rods in a manner allowing rotation between said pair of rods while holding said second ends of said pair of rods adjacent to each other; and said second ends each including parallel linear segments, said parallel linear segments also parallel with an axis of rotation of said rotating rod.

9. The device of claim 8 wherein said pair of rods are similar in shape.

10. The device of claim 8 wherein said pair of rods extend parallel with each other from said first ends to said second ends.

11. The device of claim 8 wherein a ring couples said second ends of said pair of rods together.

12. The device of claim 8 wherein said net includes stent-type netting.

13. The device of claim 8 wherein said rotating rod rotates an amount greater than 180 degrees.

14. The device of claim 8 wherein said rotating rod includes a curved segment with said net coupled to said rotating rod on at least a portion of said curved segment.

15. The device of claim 14 wherein each of said rods includes a curved segment with said net coupled to at least portions of said curved segments of each of said rods.

16. The device of claim 14 wherein said curved segment is curved with a concave side of said curved segment opposite a vessel wall when the device is located within the vessel.

17. The device of claim 8 wherein at least two grippable structures are coupled to separate ones of said first ends of said pair of rods.

18. The device of claim 17 wherein said grippable structures include a handle coupled to said first rod and a knob coupled to said second rod, said second rod being said rotating rod with rotation of said knob causing rotation of said second rod about said central axis of said second rod to cause said second rod to follow said orbital path for said second rod.

19. The device of claim 18 wherein said handle surrounds said second rod and rotatably supports said second rod without fixation to said second rod, and allowing rotation of said second rod relative to said handle, and with said first rod fixed to said handle.

* * * * *